(12) United States Patent
Szabo et al.

(10) Patent No.: US 7,757,539 B2
(45) Date of Patent: Jul. 20, 2010

(54) MODULATED PRESSURE WAVE VAPOR GENERATOR

(75) Inventors: Matthew Joseph Szabo, Stillwater, OK (US); Matthew Laurence Dock, Stillwater, OK (US); Craig Allen Aker, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 435 days.

(21) Appl. No.: 11/789,049

(22) Filed: Apr. 23, 2007

(65) Prior Publication Data
US 2007/0277585 A1 Dec. 6, 2007

Related U.S. Application Data

(60) Provisional application No. 60/794,627, filed on Apr. 24, 2006.

(51) Int. Cl.
*G01N 31/00* (2006.01)
(52) U.S. Cl. ...................................................... 73/1.05
(58) Field of Classification Search ................ 73/23.21, 73/23.25, 23.27, 31.04, 1.05
See application file for complete search history.

(56) References Cited

U.S. PATENT DOCUMENTS

| 4,540,531 | A | 9/1985 | Moy | 261/141 |
|---|---|---|---|---|
| 5,452,600 | A | 9/1995 | Davies et al. | 73/1.03 |
| 6,073,499 | A * | 6/2000 | Settles | 73/864.81 |
| 6,234,001 | B1 | 5/2001 | Sorensen et al. | 73/1.04 |
| 6,558,626 | B1 | 5/2003 | Aker et al. | 422/91 |
| 2009/0082700 | A1* | 3/2009 | Whalen et al. | 600/595 |

OTHER PUBLICATIONS

Brochure of Nomadics, Inc. entitled "A Technical Overview Fido™ Explosives Detector", 12 pp. (undated but admitted to be prior art).
Jehuda Yinon "Detection of Explosives by Electronic Noses" Analytical Chemistry, pp. 99A-105A (Mar. 1, 2003).

* cited by examiner

*Primary Examiner*—Hezron Williams
*Assistant Examiner*—Tamiko D Bellamy
(74) *Attorney, Agent, or Firm*—McAfee & Taft

(57) ABSTRACT

The current invention provides a modulated pressure wave vapor generator suitable for use outside of the laboratory. The vapor generator of the current invention produces a controlled analyte vapor sample without using bulk movement of gas. Additionally, the current invention compensates for changes in the environment to ensure discharge of the preferred volume of analyte from the vapor generator. Finally, the current invention provides a method for generating a controlled volume of analyte vapor suitable for calibrating vapor sensors.

12 Claims, 5 Drawing Sheets

MODULATED PRESSURE WAVE VAPOR GENERATOR

CROSS REFERENCE TO RELATED APPLICATION

This application claims priority from U.S. Provisional Patent Application Ser. No. 60/794,627 filed on Apr. 24, 2006, the entire contents of which are incorporated herein by reference.

STATEMENT AS TO FEDERALLY SPONSORED RESEARCH

This application was supported in part by a contract from the U.S. Army Night Vision and Electronic Sensors Directorate Contract #W909MY-04-C-0038. The United States Government may have rights in and to this application by virtue of this funding.

FIELD OF THE INVENTION

The current invention provides a vapor generator which utilizes a modulated pressure wave to generate a pre-determined amount of analyte vapor. The vapor generator compensates for changes in temperatures by changing the pressure wave used to generate the analyte sample. Additionally, the current invention provides a method of producing a controlled portion of analyte vapor without the bulk movement of gas.

BACKGROUND OF THE INVENTION

Sensors and analyzers suitable for detecting trace amounts of explosives, narcotics and other vapors of interest require calibration from time to time. Typically, these analytical devices are calibrated by measuring a controlled amount of the desired compound produced by a vapor generator. Currently available vapor generators operate by injecting a controlled amount of analyte into a stream of clean gas. In practice, the gas stream passes over a temperature controlled bed of analyte. The temperature of the bed is selected to continuously evolve a controlled amount of analyte into the passing gas stream. Thus, these systems are capable of accurately producing gas streams containing minute amounts of nearly any analyte.

Unfortunately, currently available systems have several limiting characteristics which preclude their use in the field environment. The requirement of a clean gas stream necessitates the use of a filter system or compressed bottled gas. Additionally, current vapor generators rely on precision pumps and flow meters to ensure an accurate and controlled gas flow rate. Finally, the operator must precisely control the analyte bed temperature to insure uniform evolution of the analyte into the flowing gas. As a result of these limitations, currently available vapor generation systems are complex, bulky, power hungry and expensive devices unsuitable for use in the field.

SUMMARY OF THE INVENTION

The current invention provides an apparatus for generating a controlled amount of analyte vapor while compensating for environmental changes. The apparatus of the current invention comprises a modulated pressure vapor generator having a source chamber for containing an analyte vapor. The source chamber preferably includes an orifice or pinhole opening for expelling a controlled amount of analyte vapor into the environment. Cooperating with the source chamber is a pressure transducer capable of generating an alternating air flow between the source chamber and the environment. Operation of the pressure transducer expels a controlled amount air saturated with analyte vapor through the pinhole opening into the environment. The apparatus further includes at least one environmental sensor, e.g. a temperature sensor, and a computer programmed to control the pressure transducer in response to readings obtained by the sensor and inputs from an operator.

Additionally, the current invention provides a method for generating a controlled amount of analyte vapor. In the method of the current invention, sufficient analyte is placed within a source chamber such that the air within the source chamber is saturated with analyte vapor. The source chamber is provided with or is in fluid communication with a pressure transducer. Additionally, the source chamber preferably has an orifice or pinhole opening suitable for expelling the desired analyte stream. As an initial step, the current invention provides for the characterization and standardization of the vapor generator. The characterization of the vapor generator requires a determination of the physical characteristics of the source chamber, measurement of the environmental conditions such as temperature and the determining characteristics of the pressure wave generated by the pressure transducer. In the method of the current invention, the temperature is determined by temperature sensors which cooperate with a suitably programmed computer. Following temperature characterization, pressure wave characteristics such as frequency, duty cycle, amplitude, pulse shape and number of pulses in the pulse train are determined and stored within the computer. Following the characterization steps, a controlled amount of analyte vapor can be accurately produced from the source chamber by actuation of the pressure transducer. In this step, the pressure transducer is actuated forcing air saturated with analyte from the source chamber through the pinhole as a jet. The analyte saturated air travels a short distance from the source chamber prior to stopping. Subsequently, the pressure transducer goes through an intake stroke drawing air near the pinhole back into the source chamber while leaving an analyte cloud in the environment. The final volume of analyte in the analyte cloud is controlled by the pressure pulse generated by the pressure transducer. Therefore, the temperature sensor, the controlling computer and the pressure transducer cooperate to control the generation of the analyte cloud by varying the pressure pulse of the pressure transducer. In this manner, the method of the current invention compensates for temperature variations by offering the pressure pulses over a wide dynamic range.

BRIEF DESCRIPTION OF THE DRAWINGS

FIG. 1 provides a sectional view of the vapor generator of the current invention.

FIG. 2 provides a representative view of the ejection of an analyte from the vapor generator of the current invention.

FIG. 3 provides a representative view of generation of an analyte cloud.

FIG. 4 is a sectional view of the vapor generator of the current invention fitted with an instrument interface.

FIG. 5 demonstrates sensor response under conditions of a fixed pulse train while varying the temperature.

FIG. 6 demonstrates sensor response when environmental conditions are held constant and while varying the number of pulses in the pulse train.

Figure 1:
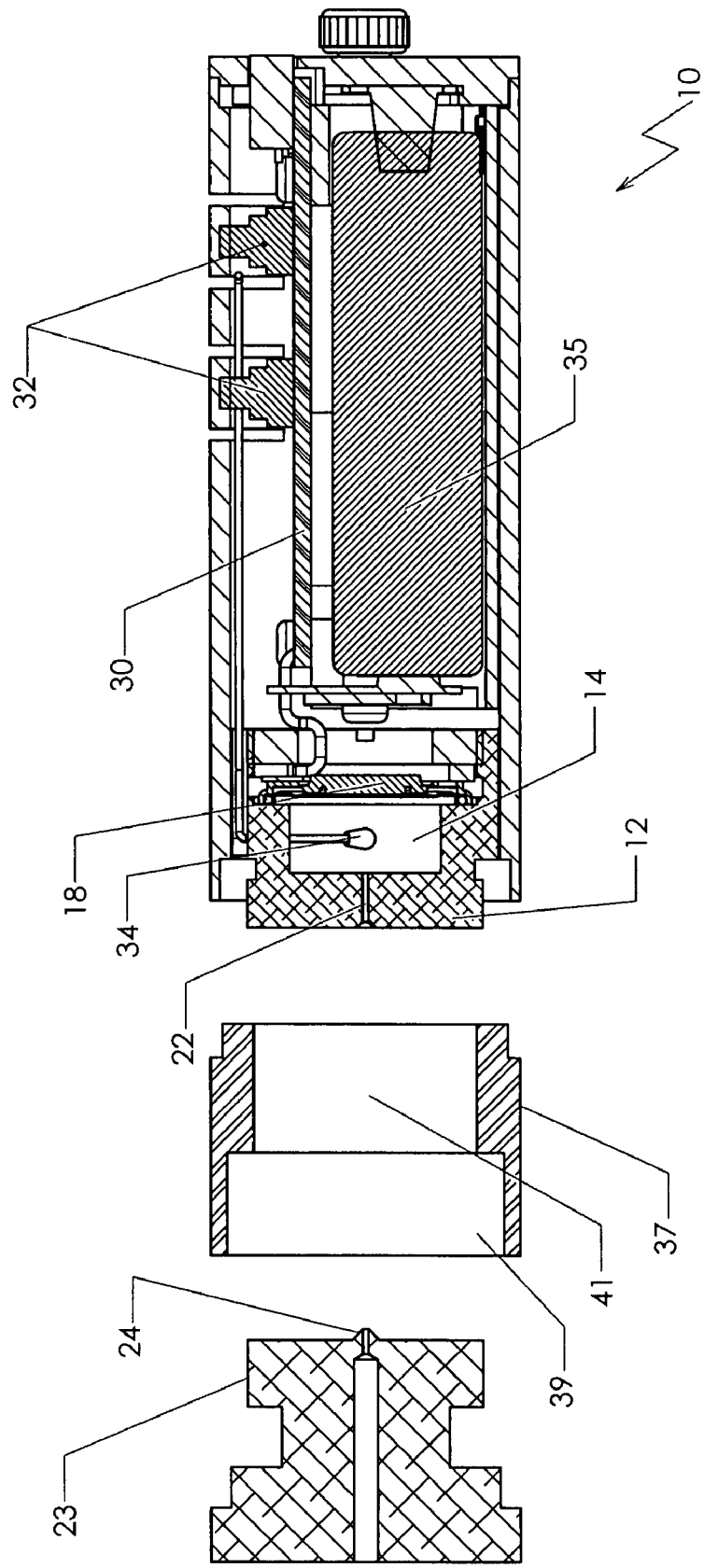
Figure 2:
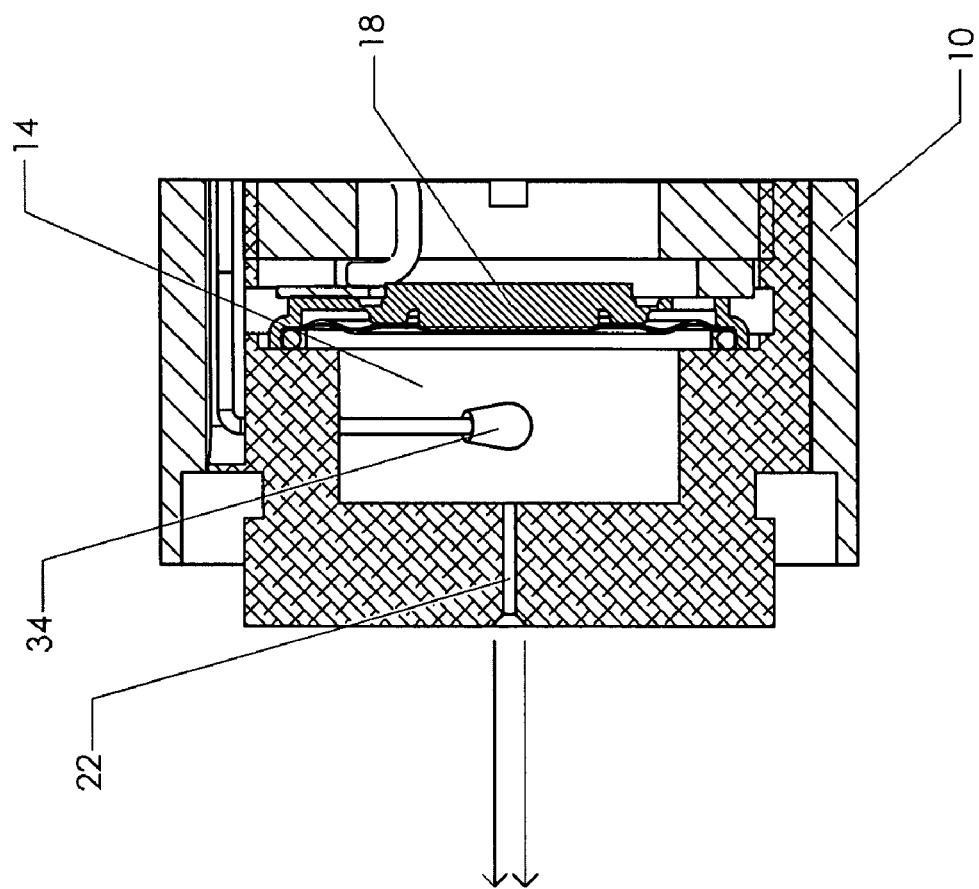
Figure 3:
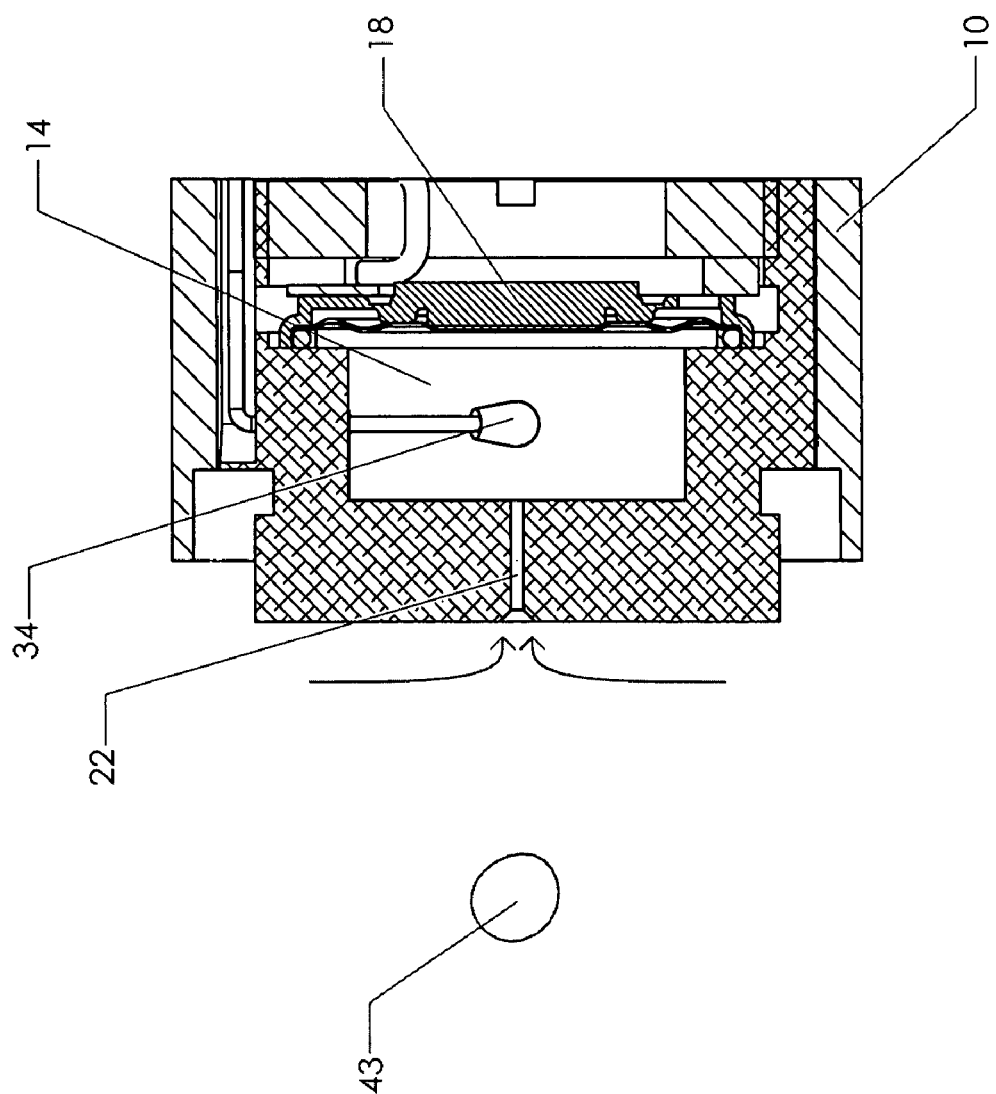
Figure 4:
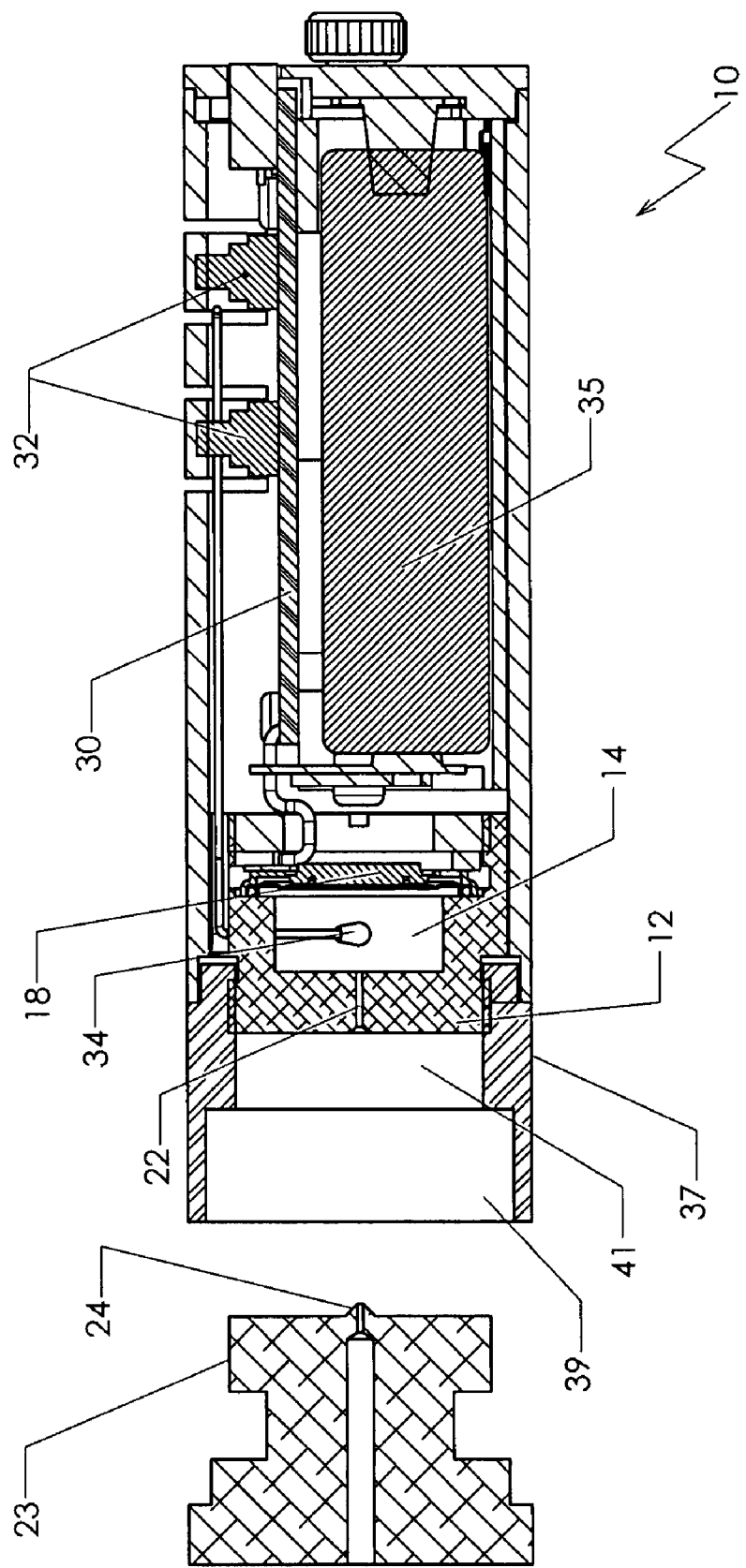
Figure 5:
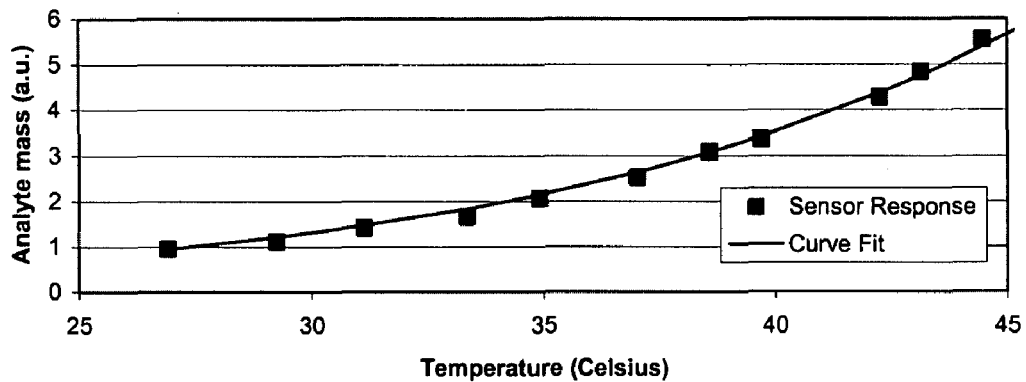
Figure 6:
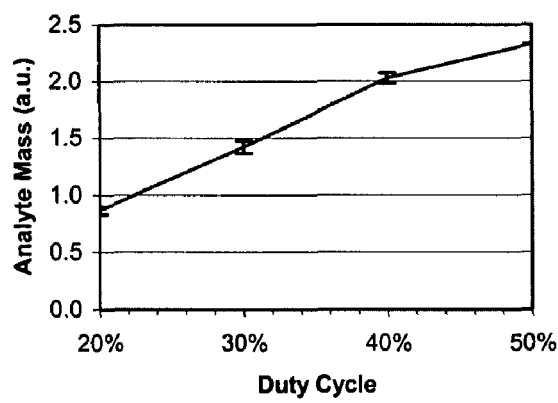
Figure 7:
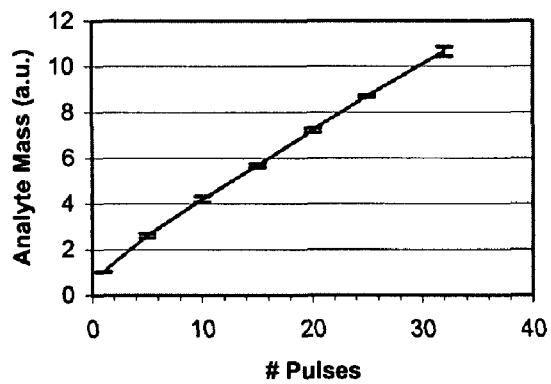

FIG. 7 demonstrates sensor response when environmental conditions are held constant and while varying the duty cycle of the pulse train.

DETAILED DISCLOSURE OF THE INVENTION

The current invention provides a pulsed pressure vapor generator suitable for use by workers in the field. For example, security guards will find the current invention useful for calibrating vapor sensors during inspections of cargo and other goods. The pulsed pressure vapor generator of the current invention overcomes the deficiencies of the prior art devices by eliminating the temperature controlled analyte bed and removing the need for bulk movement of a carrier gas. In contrast to available vapor generators, the present invention compensates for environmental changes, including but not limited to temperature and pressure, during the generation of a controlled analyte cloud.

The vapor generator of the current invention produces an analyte vapor cloud suitable for calibrating sensors or sensing devices. In particular, the vapor generator of the current invention is useful for calibrating sensors suitable for detecting explosives, narcotics, chemical warfare agents, biological warfare agents, industrial products, industrial byproducts, or their simulants. A non-limiting list of analytes useful within the vapor generator of the current invention includes TNT, RDX, DNT, amino-TNT, amino-DNT, PETN, nitrates, peroxides, musk ketone, musk xylene, nicotinamide, methyl salicylate, alcohols, and other aromatic and aliphatic hydrocarbon compounds.

With reference to the drawings, the current invention provides a modulated pressure wave vapor generator 10, referred to as vapor generator 10 herein. Vapor generator 10 comprises a source chamber 14 in fluid communication with a pressure transducer 18. A preferred pressure transducer 18 is an electric speaker. In the preferred embodiment, source chamber 14 has a pin hole opening or orifice 22. Preferably, orifice 22 is sized to produce a jet of analyte-saturated gas during operation of pressure transducer 18. In the preferred embodiment, a sealing device 23 such as a cap or plug is fitted into orifice 22 to prevent diffusion of analyte through orifice 22 during periods of non-use. Diffusion of analyte through orifice 22 may contaminate the exterior of vapor generator 10 leading to erroneous calibration of the sensor (not shown). Additionally, source chamber 14 is optionally provided with a fitting or other suitable valve or passageway (not shown) for supplying analyte to the interior of source chamber 14. Use of a fitting provides the ability to refresh the supply of analyte within source chamber 14 during operations in the field without the need for dismantling vapor generator 10.

Vapor generator 10 is controlled by a suitably programmed electronic device such as computer 30. Preferably, computer 30 controls the operation of pressure transducer 18 in response to monitored environmental conditions. Accordingly, vapor generator 10 is provided with at least one environmental sensor 34 for monitoring environmental conditions such as temperature. Environmental sensor 34 communicates the monitored condition to computer 30. In the preferred embodiment, pressure transducer 18 is provided with a power source 35. As depicted in FIG. 1, a standard AA battery is suitable for use in the current invention. Typically, power source 35 also provides power to computer 30 and other components of vapor generator 10.

Finally, in the preferred embodiment, vapor generator 10 is provided with an instrument interface 37. Instrument interface 37 may be threaded or press fit onto vapor generator 10. As shown in FIG. 1, instrument interface 37 includes a sensor port 39 and an analyte chamber 41. As depicted in FIG. 4, when instrument interface 37 is positioned on vapor generator 10, analyte chamber 41 and sensor port 39 are preferably in fluid communication with source chamber 14. However, since the primary function of instrument interface 37 is to ensure consistent positioning of the sensor (not shown) to be calibrated relative to vapor generator 10, flow of the analyte vapor through instrument interface 37 is not a necessity. Rather, instrument interface 37 may simply provide a stable consistent mechanism for reproducibly positioning a sensor relative to vapor generator 10 for calibration.

In the preferred embodiment, port 39 is a positioning receptacle suitable for receiving a sensor. Typically, a vapor sensor or similar device is positioned against or within port 39 during calibration. In this manner, instrument interface 37 provides for accurate, reproducible positioning of the sensor. Additionally, instrument interface 37 includes an analyte chamber 41. Analyte chamber 41 is defined when instrument interface 37 is pressed on or threaded on end 12 of vapor generator 10. In this arrangement, analyte chamber 41 receives the analyte vapor cloud 43 produced by vapor generator 10. Thus, instrument interface 37 enhances the accuracy of the calibration of the sensor. In the embodiment depicted in FIG. 1, sealing device 23 is sized to fit snuggly within port 39 and is placed within port 39 during periods of non-use. When instrument interface 37 is not used, tip 24 of sealing device 23 may be configured to fit within orifice 22.

The current invention further provides a method for generating a controlled amount of analyte vapor suitable for calibrating a vapor sensor. The method of the current invention will be described with reference to the Figs.

According to the preferred method of the current invention, a sufficient quantity of analyte is placed in source chamber 14 prior to assembly of pressure transducer 18 to source chamber 14. Alternatively, analyte is supplied to source chamber 14 through a fitting or valve (not shown). As noted above, resupply or replacement of analyte to source chamber 14 may be through the fitting or by removal of pressure transducer 18. The concentration of analyte in source chamber 14 is sufficient to yield a saturated atmosphere of air and analyte vapor. The air utilized in source chamber 14 is atmospheric air provided by communication between the interior of source chamber 14 and the exterior of source chamber 14 through orifice 22. Thus, the method of the current invention does not rely upon stored gas or filtered air systems.

Prior to operation of vapor generator 10, the individual components must be characterized in order to ensure the accurate generation of an analyte cloud. The characterization process provides computer 30 with the data necessary to control vapor generator 10. Factors which influence the amount of analyte generated by the vapor generator 10 include its physical characteristics, such as the size and configuration of source chamber 14, the diameter and length of orifice 22 and characteristics of the pressure transducer used; environmental factors such as temperature; and characteristics of the pulse train such as frequency, duty cycle, amplitude, pulse shape and number of pulses. The physical configuration of source chamber 14, orifice 22 and pressure transducer 18 will preferably remain constant for each vapor generator 10.

The environmental temperature is preferably monitored by environmental sensor 34. During temperature characterization, the effect of temperature differences on vapor generator 10 is determined by measuring the vapor output in response to an unvarying pressure wave over a range of temperatures.

Preferably, the temperature monitored is the temperature of the source chamber as this temperature determines the vapor pressure of the analyte.

Additionally, pressure transducer 18 is characterized by individually varying the pressure wave parameters while holding the remaining pressure wave components constant. During this step, the environmental conditions are preferably maintained constant; however, compensations for changes in the environment can be made by computer 30 using the temperature curves generated during temperature characterization. While the characterization process has been described in the order of temperature characterization followed by pressure wave characterization, one skilled in the art will recognize that pressure wave parameters may be characterized first if the temperature is maintained as a constant during such characterization.

During the temperature and pressure characterization steps, pressure pulses are generated within source chamber 14 by pressure transducer 18. The quantity of analyte ejected from source chamber 14 is measured by a suitable sensor for each characterization step. Accordingly, a series of controlled pressure pulses are generated over a range of temperatures to determine the quantity of analyte ejected from source chamber 14 for each temperature. Similarly, a series of measurements are taken while varying components of the pressure pulse, either at a constant temperature or with the sensor response corrected for temperature by computer 30 using the previously developed temperature curve. The resulting data permits controlled generation of an analyte cloud in response to changes in temperature and desired analyte volume.

FIGS. 5-7 demonstrate the calibration of one embodiment of the current invention. In FIG. 5, the pressure pulse necessary to produce the desired sample of analyte is determined over a range of temperatures. Further, in FIGS. 6 and 7 the change in percent quench demonstrates the sensor's response to changes in the pressure pulse. In FIG. 6, the duty cycle of the pressure pulse was varied while the temperature was maintained constant. In FIG. 7, the number of pulses in the pulse train was varied.

As represented by FIGS. 5-7, vapor output depends linearly on both the duty cycle and the number of pulses in the pressure wave. Thus, the characterization steps account for the parameters which directly impact the performance of vapor generator 10. Specifically, the characterization steps determine the characteristics of the pressure pulse, the analyte's vapor pressure over a range of temperatures and the source chamber's geometry. The ability of the current invention to vary the pressure pulse (or pulse train) over a wide dynamic range eliminates the need to control the temperature of source chamber 14 as the method of the current invention corrects for temperature variations by altering the pressure pulses generated by pressure transducer 18.

Following characterization, an algorithm can be created to precisely control analyte delivery into the environment. Methods for generating algorithms of this type are well known to those skilled in the art. Further, methods for programming computer 30 with such algorithms are also well known in the art. In the preferred embodiment, a calibration constant is included in the algorithm to account for variations in measurement units.

Without intending to limit the scope of the current invention, the following is one example of system characterization and the development of a control algorithm suitable for use in the method of the current invention. Those skilled in the art will recognize that other algorithms may be developed for the purposes of controlling vapor generator 10.

The characteristic equation of the vapor generator can be expressed as:

$$M=f(\sigma,\chi,\epsilon)$$

where M is the analyte mass ejected from the generator, $\sigma$ is a set of constant parameters describing the geometry of the vapor generator, $\chi$ is a set of controllable parameters governing the motion of the pressure transducer, and $\epsilon$ is a set of uncontrolled environmental parameters.

To make analysis tractable, we assume that the function is separable:

$$M=f_{\sigma_1}(\sigma_1)\cdot f_{\sigma_2}(\sigma_2)\ldots f_{\sigma_m}(\sigma_m)\cdot f_{\chi_1}(\chi_1)\cdot f_{\chi_2}(\chi_2)\ldots f_{\chi_n}(\chi_n)\cdot f_{\epsilon_1}(\epsilon_1)\cdot f_{\epsilon_2}(\epsilon_2)\ldots f_{\epsilon_p}(\epsilon_p)$$

Since the geometric parameters $\sigma_i$ are constant, the equation reduces to $$M=C_\sigma\cdot f_{\chi_1}(\chi_1)\cdot f_{\chi_2}(\chi_2)\ldots f_{\chi_n}(\chi_n)\cdot f_{\epsilon_1}(\epsilon_1)\cdot f_{\epsilon_2}(\epsilon_2)\ldots f_{\epsilon_p}(\epsilon_p)$$

where $C_\sigma$ is a constant.

To experimentally characterize the system, the first step is to determine how the output magnitude depends on the environmental variables $\epsilon$. To do this, each external variable must be externally controlled using a laboratory test jig. The output magnitude of the vapor generator can then be measured while varying one environmental parameter at a time and keeping all control parameters constant.

The data from the above set of experiments provides the basis for the "environmental correction" portion of the algorithm by providing two important kinds of information. Specifically, they identify the environmental parameters which significantly influence output magnitude and the functional dependence of the output magnitude on those parameters.

The next step is to determine how the control parameters affect output magnitude. With the environmental parameters held constant by the external test jig, each control parameter can be varied one at a time and the output magnitude measured. As with the environmental parameters, this data set provides the functional dependence of the output magnitude on the important control parameters.

The final step in determining the system characteristic equation is to measure the constant $C_\sigma$. This parameter is simply tuned such that, for a given combination of $\chi$ and $\epsilon$, the output magnitude predicted by the characteristic equation matches the measured value.

After completing the above steps, the algorithm is constructed. With the system equation known, the control problem reduces to finding a control parameter $\chi_0$ such that $$M_d=C_\sigma\cdot f(\chi_0,\epsilon_0)$$

where $M_d$ is the desired (user-selectable) output magnitude and $\epsilon_0$ gives the current environmental conditions. This equation likely has multiple solutions; the algorithm only needs to find one.

In developing an algorithm, it is useful to recognize that there are two types of control parameters. First are those parameters whose functions have an upper bound. An example is the voltage applied to the pressure transducer. Since this voltage is limited and the output magnitude increases monotonically with voltage, the function has an upper bound. Second are those parameters whose functions do not have an upper bound. An example of this type is the number of pulses. This distinction implies the following strategy:

1. Assume all parameters with upper bounds have the value of their respective upper bounds.

2. Find a combination of parameters without upper bounds which will generate an output magnitude slightly greater than desired.
3. Now vary the parameters with upper bounds to reduce the output magnitude to the desired level.

It has been found that, for certain types of pressure transducers, the output magnitude can be adequately controlled by varying only the number of pulses and the voltage applied to the transducer (i.e. the frequency and duty cycle of the pulse train can be constant). If the only environmental variable considered is temperature, the characteristic equation is:

$$M = C_\sigma \cdot f_{\chi_1}(P) \cdot f_{\chi_2}(V_f) \cdot f_{\epsilon_1}(T).$$

Let $f_{\chi_i}(\chi_i)$ have the form $$f_{\chi_1}(P) = a_0 + a_1 \cdot P + a_2 \cdot P^2$$

$$f_{\chi_2}(V_f) = b_0 + b_1 \cdot V_f + b_2 \cdot V_f^2$$

These are second-order Taylor series. More terms could be used, but solving for $\chi_i$ given $f_{\chi_i}(\chi_i)$ becomes more difficult. Furthermore, since $V_f$ is a fractional parameter, its equation is scaled such that $f_{\chi_2}(1) = 1$. We let $f_{\epsilon_1}(T)$ have the form $$f_{\epsilon_1}(T) = 10^{\alpha\left(\frac{1}{T} - \frac{1}{T_0}\right)}$$

where T is measured in Kelvin and $T_0$ is an arbitrary constant. This non-intuitive form was chosen because it matches the vapor-pressure equation for the analyte in question (TNT).

Once the constants $a_i$, $b_i$, $\alpha$, and $C_\sigma$ have been determined during system characterization, a control algorithm can be implemented. In this example, the characteristic equation can be written as $$f_{\chi 1}(P) \cdot f_{\chi 2}(V_f) = \frac{M}{C_\sigma \cdot f_{\epsilon 1}(T)}$$

For the moment, assume that $V_f$ is its maximum value of 1. Using the desired output magnitude $M_d$, the above equation reduces to $$f_{\chi 1}(P) = \frac{M_d}{C_\sigma \cdot f_{\epsilon 1}(T)},$$

which can be solved using the quadratic formula. The solution $P_c$ to this equation is then rounded up to the nearest whole number and used to find $V_f$.

$$f_{\chi 2}(V_f) = \frac{M_d}{C_\sigma \cdot f_{\epsilon 1}(T) \cdot f_{\chi 1}(P_C)}$$

As before, this equation can be solved using the quadratic formula, and the two control parameters have been found.

Utilization of vapor generator 10 subsequently entails the steps of determining the desired amount of analyte to be generated, monitoring environmental conditions using environmental sensor 34, inputting the environmental data and analyte amount into computer 30 and controlling pressure transducer 18 by operation of computer 30 to generate the desired amount of analyte vapor.

Thus, operation of vapor generator 10 is described schematically by FIGS. 2-3. Following the operator's inputting the amount of analyte to be generated into computer 30 via user interface 32, the method of the present invention determines the temperature of source chamber 14 using environmental sensor 34 and signals pressure transducer 18 to emit the necessary pressure pulse as determined by computer 30. As demonstrated by FIG. 2, when initially actuated pressure transducer 18 goes through an exhaust stroke generating a pressure pulse which forces air saturated with analyte out of source chamber 14 through orifice 22. The analyte-saturated air travels a short distance from source chamber 14 prior to the intake stroke of pressure transducer 18. FIG. 3 depicts the cycling of pressure transducer 18 to an intake stroke which subsequently draws air near orifice 22 into source chamber 14 leaving a cloud 43 of analyte in the environment. Resulting analyte cloud 43 may be used to calibrate vapor sensors. For example, explosives sensors may be adequately calibrated to detect trace amounts of explosives when the analyte stored in source chamber 14 is TNT.

Preferably, when calibrating a sensor, an instrument interface 37, depicted in FIGS. 1 and 4 and described above, is used. Instrument interface 37 ensures that a sensing device is consistently calibrated by providing a standard alignment between the sensing device and vapor generator 10. In the embodiment depicted in FIGS. 1 and 4, during calibration the sensor is positioned against or within port 39 of instrument interface 37 prior to generation of analyte cloud 43, thereby ensuring a consistent relationship between vapor generator 10 and the sensor. Following generation of analyte cloud 43, the sensor is calibrated to reflect the known quantity of analyte within the cloud. If instrument interface 37 is used during the calibration process, analyte cloud 43 is confined within analyte chamber 41 by vapor generator 10 and the sensor positioned adjacent to or within port 39, thereby enhancing the accuracy of the calibration of the sensor. While use of instrument interface 37 is preferred, satisfactory results can be achieved without use of instrument interface 37.

Other embodiments of the current invention will be apparent to those skilled in the art from a consideration of this specification and/or practice of the invention disclosed herein. Accordingly, the foregoing specification is considered merely exemplary of the current invention. The true scope of the current invention is defined by the following claims.

We claim:

1. A method for generating a controlled amount of analyte vapor comprising:
- providing a vapor generator comprising a source chamber having an orifice, wherein the atmosphere within said source chamber comprises atmospheric air, a pressure transducer in fluid communication with said source chamber, a temperature sensor suitable for monitoring the temperature of said source chamber;
- placing an analyte within said source chamber;
- characterizing temperature change effects upon said vapor generator;
- characterizing said source chamber;
- characterizing said pressure transducer;
- using said pressure transducer to generate a pressure wave thereby forcing air carrying analyte vapor from said source chamber through said orifice wherein said pressure transducer is controlled to compensate for temperature changes of said source chamber thereby generating a controlled amount of said analyte vapor.

2. The method of claim 1, further comprising the step of continuing to operate said pressure transducer to draw air from the exterior of said source chamber into said source chamber.

3. The method of claim 1, wherein said step of characterizing said source chamber comprises the steps of determining the size and configuration of said source chamber and said orifice.

4. The method of claim 1, wherein said step of characterizing said pressure transducer comprises the steps of generating controlled pressure waves over a range of temperatures.

5. The method of claim 1, wherein said step of characterizing said pressure transducer comprises the steps of maintaining a constant temperature while generating a series of pressure waves wherein one parameter of said series of pressure waves is varied and the remaining parameters of said series of pressure waves are held constant.

6. The method of claim 1, further comprising the step of monitoring the temperature of said source chamber and wherein said step of characterizing temperature change effects upon said vapor generator comprises the steps of measuring vapor output from said source chamber in response to an unvarying pressure wave while varying the temperature of said source chamber and monitoring the temperature of said source chamber with said temperature sensor.

7. The method of claim 1, wherein the step of characterizing said pressure transducer comprises the steps of maintaining a constant temperature while generating a series of pressure waves wherein one parameter of said series of pressure waves is varied and the remaining parameters of said series of pressure waves are held constant.

8. The method of claim 7, wherein the pressure wave parameters include: frequency, duty cycle, amplitude, pulse shape and number of pulses.

9. The method of claim 1, further comprising the step of using said analyte vapor to calibrate a vapor sensor.

10. The method of claim 1, wherein said pressure transducer is positioned within said source chamber.

11. A method for generating a controlled amount of vapor comprising:

placing an vapor producing material in a source chamber, wherein the interior of said source chamber is in fluid communication with the exterior environment and wherein the atmosphere within said source chamber comprises atmospheric air;

monitoring temperature conditions within said source chamber; and, passing a pressure wave through said source chamber thereby producing a vapor cloud to the exterior of said source chamber wherein said pressure wave is controlled in response to monitored temperature conditions; and, varying the temperature of said source chamber while generating said vapor cloud thereby determining the effect of changes in temperature on the generation of said vapor cloud.

12. The method of claim 11, wherein a pressure transducer is associated with said source chamber and said pressure transducer generates said pressure wave.

* * * * *